(12) United States Patent
Jobling et al.

(10) Patent No.: US 6,635,756 B1
(45) Date of Patent: Oct. 21, 2003

(54) STARCH OBTAINABLE FROM MODIFIED PLANTS

(75) Inventors: Stephen Alan Jobling, Eaton Socon (GB); Roger John Westcott, Wellingborough (GB); Gerhard Peter Schwall, Schmallenberg (DE); Catherine Rosemary Martin, Norwich (GB); Elizabeth Anne Edwards, Norwich (GB); Alison Mary Smith, Norwich (GB)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 09/719,771

(22) PCT Filed: Jun. 15, 1999

(86) PCT No.: PCT/GB99/01902
§ 371 (c)(1),
(2), (4) Date: Mar. 5, 2001

(87) PCT Pub. No.: WO99/66050
PCT Pub. Date: Dec. 23, 1999

(30) Foreign Application Priority Data

Jun. 15, 1998 (GB) .............................. 98309716

(51) Int. Cl.$^7$ ......................... C08B 31/00; C08B 33/00; C08B 35/00

(52) U.S. Cl. ...................... 536/102; 536/45; 536/123.1; 536/124; 536/127; 536/128; 800/284

(58) Field of Search ....................... 536/45, 102, 123.1, 536/124, 127, 128; 800/284

(56) References Cited

U.S. PATENT DOCUMENTS 6,013,299 A * 1/2000 Haynes et al. ............... 426/549

FOREIGN PATENT DOCUMENTS

| CA | 2205118 | 5/1996 | |
|---|---|---|---|
| DE | 43 30 960 | 3/1995 | |
| DE | 44 41 408 | 5/1996 | |
| EP | 0779363 A2 * | 6/1997 | ........... C12N/15/82 |
| EP | 0 799 363 B1 | 5/1999 | |
| WO | WO 94/24292 | 10/1994 | |
| WO | WO 95/26407 | 10/1995 | |
| WO | WO 95/35026 | 12/1995 | |
| WO | WO 96/15248 | 5/1996 | |
| WO | WO 96/34968 | 11/1996 | |
| WO | WO 97/20040 | 6/1997 | |
| WO | WO 97/20936 | 6/1997 | |
| WO | WO 97/22703 | 6/1997 | |
| WO | WO 97/44472 | 11/1997 | |
| WO | WO 97/45545 | 12/1997 | |

OTHER PUBLICATIONS

Lloyd, James R. et al., "Simultaneous antisense inhibition of two starch–synthase isoforms in potato tubers leads to accumulation of grossly modified amylopectin", Biochem. J. 338: 515–521, 1999.

Abel et al., "Cloning and functional analysis of a cDNA encoding a novel 139 kDa starch synthase from potato (Solanum tuberosum L.)", Plant Journal 10(6):981–991, 1996.

Becker et al., "New plant binary vectors with selectable markers located proximal to the left T–DNA border", Plant Molecular Biology 20: 1195–1197, 1992.

Craig et al., "Mutations in the Gene Encoding Starch Synthase II Profoundly After Amylopectin Structure I Pea Embryos", Plant Cell 10: 413–426, 1998.

Denyer et al. "The isolation and characterization of novel low–amylose mutants of Pisum sativum L.", Plant Cell Environ. 18: 1019–1026, 1995.

Dry et al., "Characterization of cDNAs encoding two isoforms of granule–bound starch synthase which show differential expression in developing storage organs of pea and potato", Plant Journal 2(2): 193–202, 1992.

Edwards et al., "Biochemical and molecular characterization of a novel starch synthase from potato tubers", Plant Journal 8(2): 283–294, 1995.

Evans and Halsman, "The Effect of Solutes on the Gelatinization Temperature Range of Potato Starch", Stärke 34(7):224–231, 1982.

Flipse et al., "The dosage effect of the wildtype GBSS allele is linear for GBSS activity but not for amylose content: absence of amylose has a distinct influence on the physico–chemical properties of starch", Theor. Appl. Genet. 92: 121–127, 1996.

Gao et al., "Characterization of dull1, a Maize Gene Coding for a Novel Starch Synthase", Plant Cell 10, 399–412, 1998.

Hanashiro et al., "A periodic distribution of the chain length of amylopectin as revealed by high–performance anion–exchange chromotography", Carbohydrate Research 283: 151–159, 1996.

Harn et al., "Isolation and characterization of the zSSIIa and zSSIIb starch synthase cDNA clones from maize endosperm", Plant Mol. Biol. 37: 639–649, 1998.

Hovenkamp–Hermelink et al., "Isolation of an amylose–free starch mutant of the potato (Solanum tuberosum L.)", Theor. Appl. Genet. 75: 217–221, 1987.

(List continued on next page.)

Primary Examiner—James O. Wilson
Assistant Examiner—Patrick Lewis
(74) Attorney, Agent, or Firm—Karen G. Kaiser

(57) ABSTRACT

A starch obtained from a plant modified by manipulating the activity of a combination of plant enzymes having starch synthase activity, in particular starch synthase II (SSII) and starch synthase III (SSIII). Modified plants, their use as food products and starch, in particular obtained from a modified potato plant, having unexpected properties and uses thereof are also disclosed.

9 Claims, 13 Drawing Sheets

OTHER PUBLICATIONS

Kossmann et al., "Starch Biosynthesis and Modification of Starch Structure in Transgenic Plants", Macromol. Symp.12;0 29–38, 1997.

Marshall et al., "Identification of the Major Starch Synthase in the Soluble Fraction of Potato Tubers", Plant Cell 8, 1121–1135, 1996.

Morrison and Laignelet, "An Improved Colorimetric Procedure for Determining Apparent and Total Amylose in Cereal and Other Starches", Journal of Cereal Science 1: 9–20, 1983.

Munyikwa et al.. "Cassava starch biosynthesis: new avenues for modifying starch quantity and quality", Euphytica 96: 65–75, 1997.

Murashige and Skoog, "A Revised Medium for Rapid Growth and Bio Assays with Tobacco Tissue Cultures", Physiol. Plant 15: 473–497, 1962.

Ring et al., "The Gelation and Crystallisation of Amylopectin", Carbohydrate Research 162: 277–293, 1987.

Shi et al., "Molecular Structure of a Low–Amylopectin Starch and Other High–Amylose Maize Starches", Journal of Cereal Science 27: 289–299, 1998.

Shure et al. , "Molecular Identification and Isolation of the Waxy Locus in Maize", Cell 35, 225–233, 1983.

Stute, Rolf, "Hydrothermal Modification of Starches: The Difference between Annealing and Heat/Moisture—Treatment", Stärke 4: 205–214, 1992.

Tomlinson et al., "Major differences in isoform composition of starch synthase between leaves and embryos of pea (Pisum sativum L.)", Planta 204: 86–92, 1998.

* cited by examiner

28 & 29

CONTROL (25 & 26)

STARCH OBTAINABLE FROM MODIFIED PLANTS

This application is a 371 of PCT/GB99/01902.

FIELD OF THE INVENTION

The present invention relates to plant modification, especially modification by manipulating the activity of a combination of plant enzymes having starch synthase activity to alter the nature of starch obtainable from the plant. In particular, it relates to manipulation of activity of the plant enzymes starch synthase II (SSII) and starch synthase III (SSIII), modified plants obtained thereby and their use as food products. The invention also relates to starch having novel properties and to uses thereof.

BACKGROUND OF THE INVENTION

Starch is of importance in a variety of food and other applications, such as in the paper, textiles and adhesives industries. Commonly, native starches obtained from storage organs of plants such as cereal endosperms, potato tubers and pea embryos are further modified, generally by either chemical or physical means, to produce starches having improved properties more suited to the intended application. Commercial interest has been directed, in particular, to methods for modifying or manipulating the temperature at which onset of gelatinisation occurs (that is, the process of collapse or disruption of molecular order within the starch granules when aqueous suspensions of starch granules are heated, causing the granules to swell and absorb water). Methods for manipulating the gelatinisation temperature of starch which have been described in the literature include the use of additives (see, for example, Evans et al, Starke, 34, 224–231, 1982) or chemical or physical pre-treatments (see Stute, Starke, 44, 205–21, 1992).

It would be desirable commercially to provide plants which intrinsically produce starches having the desired properties, thereby obviating the need for additional, costly and generally inefficient, modification steps. To this end, considerable interest has been expressed in the art in studying the starch biosynthetic pathway in plants, more particularly in the potato, with the aim of modifying the plant genome to produce starches with novel and advantageous properties.

Approaches to modifying the starch biosynthetic pathway in plants using recombinant DNA technology have recently been described in the literature. In particular, methods based on manipulating the activity of plant enzymes having either starch branching or starch synthase activity, generally regarded as the most important starch-synthesising enzymes, have been studied.

WO 96/34968, published November 1996, discloses a nucleotide sequence encoding an effective portion of a Class A starch branching enzyme (SBE) obtainable from potato plants, which sequence can be introduced, conveniently linked in an antisense orientation to a suitable promoter and preferably together with an effective portion of a sequence encoding a Class B starch branching enzyme, into a plant to alter the characteristics of the plant. It is disclosed that starch extracted from a plant so transformed has a viscosity onset temperature (which gives an indication of the onset of the gelatinisation process) which is elevated by around 10 to 25° C. compared to starch extracted from a similar but unaltered plant.

Isoforms of starch synthase are found in the storage organs of most species of plants and there is currently much interest in characterising them and studying their role in starch synthesis. In pea for instance, the low amylose locus (lam) was shown to be a mutation in the granule-bound starch synthase I (GBSS I) gene (Denyer et al Plant Cell Environ. 18,1019–1026, 1995) and very recently, the rug5 locus was shown to be a mutation in the major soluble isoform of starch synthase (SSII) (Craig et al Plant Cell 10, 413–426, 1998). In maize, the waxy gene encoding the granule-bound starch synthase I (GBSS I) has been cloned (Shure et al Cell 35, 225–233, 1983) and the recent cloning of the dullI gene identifies that locus as a starch synthase, most likely SSII (Gao et al Plant Cell 10, 399–412, 1998). In addition, several recent patent publications describe the cloning of starch synthases from maize (WO 97/44472, WO 97/20936) and wheat (WO 97/45545). The role of each isoform in the control of starch synthesis and structure is unclear at present since the contribution of each isoform to the total activity varies considerably between species.

Marked effects on the properties of starch, in particular a reduction in the viscosity onset temperature compared to untransformed material, have been observed when potato plants are modified by manipulation of one particular starch synthase enzyme, now designated as starch synthase III (SSIII) (see EP-A-0779363, National Starch and Chemical Investment Holding Corporation, published June 1997, and Marshall et al, Plant Cell, 8, 1121–1135, 1996). Here, a reduction in the onset temperature for gelatinisation of starch extracted from transformed potato plants of at least 5° C. compared to starch extracted from equivalent, non-transformed plants was reported. In addition to the differences in starch properties, altered starch granule morphology and reductions in soluble starch synthase activity in the order of 80% were reported.

WO 96/15248 (Institut Fur Genbiologische Forschung Berlin GmbH), published May 1996, discloses potato plants transformed with a portion of either one of two cDNA clones, denoted SSSA and SSSB, which are said to encode isoforms of potato soluble starch synthases.

Starch synthase III (SSIII), a largely soluble isoform having a molecular mass as judged by SDS-PAGE in the range of 100–140 kDa is one of three isoforms of starch synthase, each encoded by a different gene, which have been purified in developing potato tubers. The other isoforms which have been described and characterised are a granule bound starch synthase of approximately 60 kDa, designated granule bound starch synthase I (GBSSI, also known as the waxy protein), see, for example, Hovenkamp-Hermelink et al, (Theor. Appl. Genet., 7, 217–221, 1987), and starch synthase II (SSII, formerly known as GBSSII), see, for example, Edwards et al, (Plant J., 8, 283–294, 1995) and Marshall et al (above), which isoform is found in both soluble and granule bound forms and has an apparent molecular weight of approximately 78 kDa. Potato plants either lacking these other isoforms or having reduced isoform activity have been generated and the effects on the properties of the starch obtained therefrom have been studied.

Elimination of GBSSI activity through mutagenesis resulted in a tuber starch with no amylose whereas reduction of its activity through expression of antisense RNA leads to tuber starches with reduced levels of amylose. The physical properties of the starches so produced are similar to those low- or zero-amylose starches known from other sources such as the waxy mutants of cereals (see, for example, Flipse et al, Theor. Appl. Genet., 92, 121–127, 1996).

Reductions in the amount of both soluble and granule-bound SSII protein via expression of antisense RNA were found to have little or no effect on the total (soluble and granule-bound) starch synthase activity of the tuber, the amount of starch, or the amylose to arnylopectin ratio of the starch (see Edwards et al, 1995 and Koβmann et al Macromol. Symp. 120, 29–38, 1997). The present inventors have also found that there is little effect on the physical properties of the starch from such tubers.

There remains a continuing need for the development of improved methods for modulating or manipulating starch biosynthesis in plants with the aim of producing transformed plants and starches having improved properties. In particular, there is considerable commercial interest in the development of improved methods for producing transformed plants providing starches having a reduced viscosity onset temperature compared to currently available starches as this would be advantageous in allowing for the use of milder processing conditions and reduced energy use. Benefits resulting from the use of such plants in the preparation of food products include improvements in food quality, reduction of off flavours or volatiles and improvements in colour.

SUMMARY OF THE INVENTION

Accordingly, in a first aspect the invention provides a method of modifying one or more characteristics of a plant comprising introducing into the plant a combination of sequences, each sequence comprising a gene encoding an enzyme having starch synthase activity, or a sequence functionally equivalent thereto or an effective part thereof, each sequence being operably linked to a promoter so as to inhibit the expression of corresponding endogenous genes in the plant. The introduced sequences may inhibit the expression of the corresponding endogenous genes in the plant, either by means of sense suppression, or by means of antisense inhibition, both of which phenomena are known to those skilled in the art. The introduced sequences may inhibit the expression of the corresponding endogenous genes in the plant at the nucleic acid (DNA and/or RNA) and/or amino acid level. Typically the combination comprises sequences encoding two starch synthase genes, or sequences functionally equivalent thereto.

Generally, the characteristic of the plant altered by the method will include the level of activity of one or more starch synthases in the plant. In addition the physical and/or chemical properties of starch produced by the plant may be altered.

In another aspect, the invention provides a plant which has been modified by the method defined above and its use in the preparation of a food product.

Progeny of a plant according to the invention and any part thereof are also provided.

The invention also provides starch obtained or obtainable from a plant according to the invention or the progeny of such a plant and the use thereof, for example in the preparation or processing of foodstuffs, or in the paper, textile or adhesive industries. In a further aspect, the invention provides a method of modifying starch comprising modifying a plant by the method defined above and extracting therefrom starch having modified properties compared to starch extracted from equivalent, but unmodified, plants.

The invention further provides a DNA construct comprising a combination of sequences, each sequence comprising a gene encoding an enzyme having starch synthase activity, or a functionally equivalent sequence thereof or an effective part thereof, each sequence being operably linked to a promoter. Plants comprising such a construct or any part of the progeny thereof are also included within the scope of the invention.

As used herein, "plant" means a whole plant or part thereof, or a plant cell or group of plant cells. Parts of a plant typically include storage organs, such as potato tubers, cereal endosperms or pea embryos and seeds.

A "gene" is a DNA sequence encoding a protein, including modified or synthetic DNA sequences or naturally occurring sequences encoding a protein, and excluding the 5' sequence which drives the initiation of transcription.

A sequence functionally equivalent to a sequence encoding an enzyme having starch synthase activity includes any sequence which, when placed under the control of a suitable promoter, inhibits the expression of the corresponding, naturally occurring endogenous gene. Functionally equivalent sequences are intended to include those sequences exhibiting at least 60% nucleotide homology, preferably at least 80%, more preferably at least 90% homology with the sequence of a naturally occurring endogenous plant starch synthase gene. Such equivalent sequences are generally able to hybridise under standard laboratory conditions (see for example, Sambrook et al, Molecular Cloning: A Laboratory Manual, 2nd Edition, hereinafter "Sambrook") with the –ve strand of a naturally occurring endogenous plant starch synthase gene.

Preferred starch synthase genes for use in the method of the invention are the starch synthase II gene from potato (Edwards et al., 1995) and the starch synthase III gene from potato (Abel et al., Plant J. 10, 9810991; Marshall et al., 1996). Functional equivalents of the potato SSII gene have been described for pea (Dry et al., 1992 Plant J. 2, 193–202); cassava (Munyikwa et al., 1997 Euphytica 96, 65–75) and maize (Harn et al., 1998 Plant Mol. Biol. 37, 639–649). Functional equivalents of the potato SSIII gene have been described for maize (Gao et al., 1998 Plant Cell 10, 399–412) and pea (Craig et al., 1998 Plant Cell 10, 413–426; Tomlinson et al., 1998 Planta 204, 86–92).

In addition, functionally equivalent sequences particularly include those which are antisense equivalents of the sequence encoding an enzyme having starch synthase activity. Such antisense equivalents are therefore generally able to hybridise with the sense (+ve) strand of a naturally occurring endogenous plant starch synthase gene.

"Operably linked to a promoter" means that the sequence is positioned or connected to the promoter in such a way to ensure transcription of the sequence. The promoter is any sequence sufficient to allow the DNA to be transcribed. After the gene and promoter sequences are joined, upon activation of the promoter, the gene will be expressed.

An "equivalent, unmodified" plant is a plant which has a substantially identical genotype to a modified plant of the invention excepting the introduced sequences present in the plant of the invention. Also included within this definition are plants comprising the introduced sequences but which do not exhibit reduced starch synthase activity.

A "construct" is a polynucleotide comprising nucleic acid sequences not normally associated in nature.

BRIEF DESCRIPTION OF THE DRAWINGS

The present invention may be more fully understood by reference to the following description, when read together with the accompanying drawings in which.

DETAILED DESCRIPTION OF THE INVENTION

Figure 1:
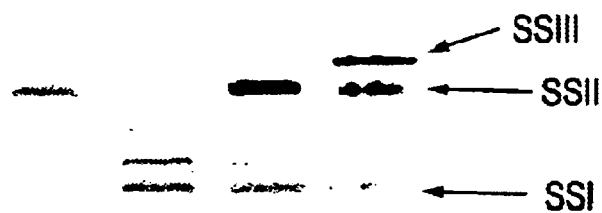
FIG. 1 is a photograph of showing the results of native gel electrophoresis of soluble extract from developing Desiree tubers stained for starch synthase activity, showing extracts of tubers of (left to right) SSIII antisense (line 18), SSII/SSIII antisense (line 21), SSIII antisense (line 9), and control line. All lanes contain material extracted from the same fresh weight of tuber. The SSIII band is absent in all three transgenic lines and the SSII band is absent in the SSII/SSIII antisense line.

The present invention is based in part on the finding that one or more characteristics of a plant may be modified by introducing into the plant a combination of fragments of genes encoding enzymes having starch synthase activity in an antisense orientation with respect to a promoter so as to affect expression of corresponding endogenous genes in the plant. Advantageously, by means of the invention, the physical and/or chemical properties of starch obtainable from the plant may be modified.

In particular, the present inventors have surprisingly found that starch extracted from a plant transformed by introduction of an SSII/SSIII combination operably linked in the antisense orientation to a suitable promoter according to the invention, or the progeny of such a plant, has a viscosity onset temperature, as determined by viscoamylograph, which is significantly reduced compared to the effects predicted by reducing the two isoforms individually or to equivalent, unmodified plants.

For the purposes of the present invention, viscoamylograph conditions are understood to pertain to analysis of a 10% (w/w) aqueous suspension of starch at atmospheric pressure using a Newport Scientific Rapid Visco Analyser with a heating profile of: holding at 50° C. for 2 minutes (step 1), heating from 50 to 95° C. at a rate of 1.5° C. per minute (step 2), holding at 95° C. for 15 minutes (step 3), cooling from 95 to 50° C. at a rate of 1.5° C. per minute (step 4), and then holding at 50° C. for 15 minutes (step 5). The viscosity onset temperature is the temperature at which the starch exhibits a sudden, marked increase in viscosity from baseline levels during viscoamylograph, and is a term well-known to those skilled in the art. In particular, the viscosity onset temperature may be defined as the temperature at which viscosity is at least 50% higher than at lower temperatures (above 50° C.). Set-back viscosity may be defined as the viscosity of the starch suspension at the end of step 5 of the viscoamylograph.

The method of the invention calls for a combination of genes encoding enzymes having starch synthase activity or a sequence functionally equivalent thereto or an effective part thereof. A particularly suitable combination of genes for use according to the invention comprises a gene (or sequence functionally equivalent thereto) encoding starch synthase II (SSII) (especially the gene for potato SSII), together with a gene (or sequence functionally equivalent thereto) encoding starch synthase III (SSIII) (especially the gene for potato SSIII) but it will be appreciated that the invention is not limited to this combination and extends to the use of any combination of genes encoding enzymes having starch synthase activity, or functionally equivalent sequences or effective parts thereof.

It will further be appreciated that the sequence encoding the starch synthase enzyme may be a synthetic sequence (e.g. synthesised in vitro) but conveniently will be a genomic or cDNA clone.

Introduction of a combination of sequences according to the invention into a plant has been found to affect the characteristics of the plant, in particular the properties of the starch obtainable therefrom. The combination of sequences may be operably linked to a promoter active in a plant in either the sense or, more preferably, antisense orientation. Either antisense inhibition or sense suppression could be used in order to alter one or more characteristics of the plant into which the sequence is introduced. It will be appreciated that neither a full length nucleotide sequence nor a native sequence is required in order to modify the characteristics of the plant but that fragments of the sequence ("an effective part") may be found by simple trial and error which have the same functional effect. For example, by substituting the proposed alternative sequence for the SSII sequence in the construct pSJ42 (described below) or the SSIII sequence in the construct pSJ119 (described below), and then following the teaching of the present specification, it can readily be ascertained if the alternative sequence is suitable for performing the invention.

An "effective part" will normally comprise at least 200 bp, preferably 300 bp–3 Kb. Conveniently an effective part will comprise between 500 bp and 1 Kb of sequence.

Each of the introduced sequences will be operably linked to a promoter sequence. In one embodiment, a single promoter will transcribe each of the introduced sequences (i.e. promoter-sequence 1-sequence 2), wherein sequence 1 may be said to be directly operably linked to the promoter, and sequence 2 may be said to be indirectly operably linked to the promoter. Alternatively, each introduced sequence may be directly operably linked to one or more separate promoters (i.e. promoter 1-sequence 1-promoter 2-sequence 2). The respective separate promoters may be the same, or may be different. Further, if desired, one sequence could be linked to its promoter in the sense orientation and one sequence linked (directly or indirectly) in the antisense orientation. For convenience, both sequences will normally be linked in the same (preferably antisense) orientation.

Suitable promoters, which may be homologous or heterologous to the introduced gene sequence, useful for expression in plants are well known to those skilled in the art. Promoters for use according to the invention may be inducible, constitutive or tissue-specific or have various combinations of such characteristics. Useful promoters include but are not limited to constitutive promoters such as cauliflower mosaic virus (CaMV) 35S promoter, or more particularly the double enhanced cauliflower mosaic virus promoter, comprising two CaMV 35S promoters in tandem, and tissue-specific promoters such as the potato tuber specific patatin promoter or granule bound starch synthase promoter. Use of a tissue-specific promoter would advantageously allow for expression of the operably linked sequences primarily in those tissues where starch synthesis or starch storage mainly occurs.

The method according to the invention suitably extends to any plant which is a source of starch, including crop plants such as cereals, pulses, maize, cassava, wheat, potatoes, rice, barley, tomato, pea and other root, tuber or seed crops. Preferably, the plant into which the sequence according to the invention, is introduced, will comprise endogenous natural starch synthase genes exhibiting sequence homology, desirably in the order of at least 70%, with the respective introduced sequence. A particularly preferred plant is the potato.

Where homologous starch synthase isoforms for a particular plant are known, these sequences may suitably be used directly in antisense or sense suppression methods according to the invention. Alternatively, it should be possible to isolate functionally equivalent sequences from particular plants of interest by isolating MRNA and screening (by means, for example, of hybridisation or PCR) cDNA obtained therefrom using a probe DNA sequence based on, for example, known potato starch synthase genes.

Plants incorporating a combination of genes encoding enzymes having starch synthase activity, or sequences functionally equivalent thereto, operably linked in a sense or antisense orientation to one or more suitable promoters according to the invention may be produced by crossing one plant comprising one of the enzyme genes (or a sequence functionlly equivalent thereto) with another plant comprising another enzyme gene (or sequence functionally equivalent thereto), using conventional cross-breeding techniques.

Alternatively, a plant according to the invention may be produced by introducing a gene encoding one of the enzyme genes (or a sequence functionally equivalent thereto) of the combination, operably linked in a sense or antisense orientation to a suitable promoter using conventional plant transformation methods, and the transformed plant subsequently further modified by introducing a further gene (or a sequence functionally equivalent thereto) of the combination, also operably linked in a sense or antisense orientation to a suitable promoter, so as to give a doubly transformed plant in accordance with the invention. Both transformations may be effected substantially simultaneously or, more preferably, sequentially. Sequential performance of the transformations may be preferred as it allows for selection of plants whose properties have been favourably altered by introduction of the first sequence of the combination, increasing the likelihood of obtaining desirable results following performance of the second transformation.

It will be appreciated that if the plant already has a low level of activity of one isoform of starch synthase, for example if it already comprises a sense or antisense sequence which inhibits the activity of one starch synthase enzyme, then a similar effect on the characteristics of the plant may be achieved by introducing a sense or antisense sequence inhibiting another starch synthase enzyme to produce a plant wherein the activity of both isoforms is inhibited.

Yet a further manner of preparing a plant in accordance with the invention is to prepare a single nucleic acid construct, which construct comprises the combination of sequences, to be introduced into the plant in a single transformation reaction. This has the advantage of requiring only a single transformation, but does not allow for the selection of favourable transformant plants following introduction of a first sequence of the combination.

Preferably, DNA constructs for incorporation into a plant according to the invention are comprised within a vector, most suitably an expression vector adapted for expression in an appropriate plant cell. It will be appreciated that any vector capable of producing a plant comprising the introduced DNA sequences will be sufficient for the purposes of the invention. Suitable vectors are well known to those skilled in the art.

Transformation techniques for introducing the sequences according to the invention into the plant are well known in the art and include such methods as microinjection, using polyethylene glycol, electroporation or high velocity ballistic penetration. A preferred method for use according to the present invention relies on Agrobacterium-mediated transformation. Whole transgenic plants may be regenerated from transformed plant cells by conventional methods and the transgenic plants propagated and crossed to provide homozygous lines. Such plants may produce seeds containing genes for the introduced trait and can be grown to produce plants that will produce the selected phenotype. It will be appreciated that neither the particular choice of transformation system, nor the choice of technique for plant regeneration is essential to or a limitation of the invention.

In accordance with a particular embodiment of the invention, there is provided a plant, particularly a potato plant, or the progeny thereof, modified by the method defined above containing starch which when extracted from the plant has a viscosity onset temperature, as judged by viscoamylograph under the conditions defined previously, which is reduced by at least 10° C., preferably at least 12° C., compared to starch extracted from equivalent, unmodified plants. In particular, the invention provides for starch, extracted from a modified potato plant or the progeny thereof, which starch has a viscosity onset temperature, as judged by viscoamylograph under the conditions defined previously, of less than 55° C.

There is further provided a plant, particularly a potato plant, or the progeny thereof modified by the method above containing starch which, when extracted from the plant, has a reduced endotherm onset temperature, as determined by differential scanning calorimetry (DSC), compared to starch extracted from equivalent, unmodified plants. Typically, the endotherm onset temperature is reduced by at least 15° C. and is less than 44° C. Potato starches as defined above have a substantially normal apparent amylose content in the region of 25–30% amylose as judged by iodine staining according to the method of Morrison et al (J. Cereal Sci, 1, 9–20, 1983). By way of explanation, the iodine staining method of Morrison et al measures the apparent amylose content of starch. In actuality, iodine is bound not only by amylose, but also by long chain amylopectin molecules (i.e. those having a helix at least 15 glucose residues long). Thus, at least some iodine binding is due to long chain amylopectin molecules. As described further below, the actual amylose content of starch from plants obtained by the method of invention is normally increased. However, this is typically accompanied by a decrease in long chain amylopectin content, such that the apparent amylose content, as judged by the method of Morrison et al., is not significantly altered.

There is further provided a plant, particularly a potato plant, or the progeny thereof modified by the method above containing starch, which when extracted from the plant, has an altered molecular structure as determined by gel permeation chromatography or high performance anion exchange chromatography (HPEAC), compared to starch extracted from equivalent, unmodified plants. Typically the ratio of the amylose to amylopectin peaks will have substantially reversed so that there is more amylose than amylopectin.

In particular the invention provides native starch (that is, starch which has not been chemically or physically modified in vitro) obtainable from a plant modified by the method of the invention, or the progeny of such a plant, having an altered chain length distribution, as determined by gel permeation chromatography and/or HPEAC, compared to starch obtained from an equivalent unmodified plant. In particular the invention provides such starch from a potato plant. The invention especially provides starch in which, compared to starch from an equivalent unmodified plant, there is an increase in the amount of short chain lengths (DP 6–12), and/or a decrease in the amount of long chain lengths (DP 15–24).

The following examples are provided by way of illustration only.

DNA manipulations were performed using standard procedures well known in the art as described, for example, in Sambrook unless otherwise indicated.

All documents mentioned herein are incorporated by reference.

EXAMPLE 1

A) Plant Material

Potato tubers (*Solanum tuberosum L.*) of cultivar Desiree (developing) were used. The tubers were grown in pots of soil based compost (25 cm diameter) in a greenhouse with minimum temperature of 12° C. and supplementary lighting in winter and freshly harvested for the experiments from actively growing plants.

B) Plant Transformation

1. Construction of Antisense Transformation Vector

Figure 6:
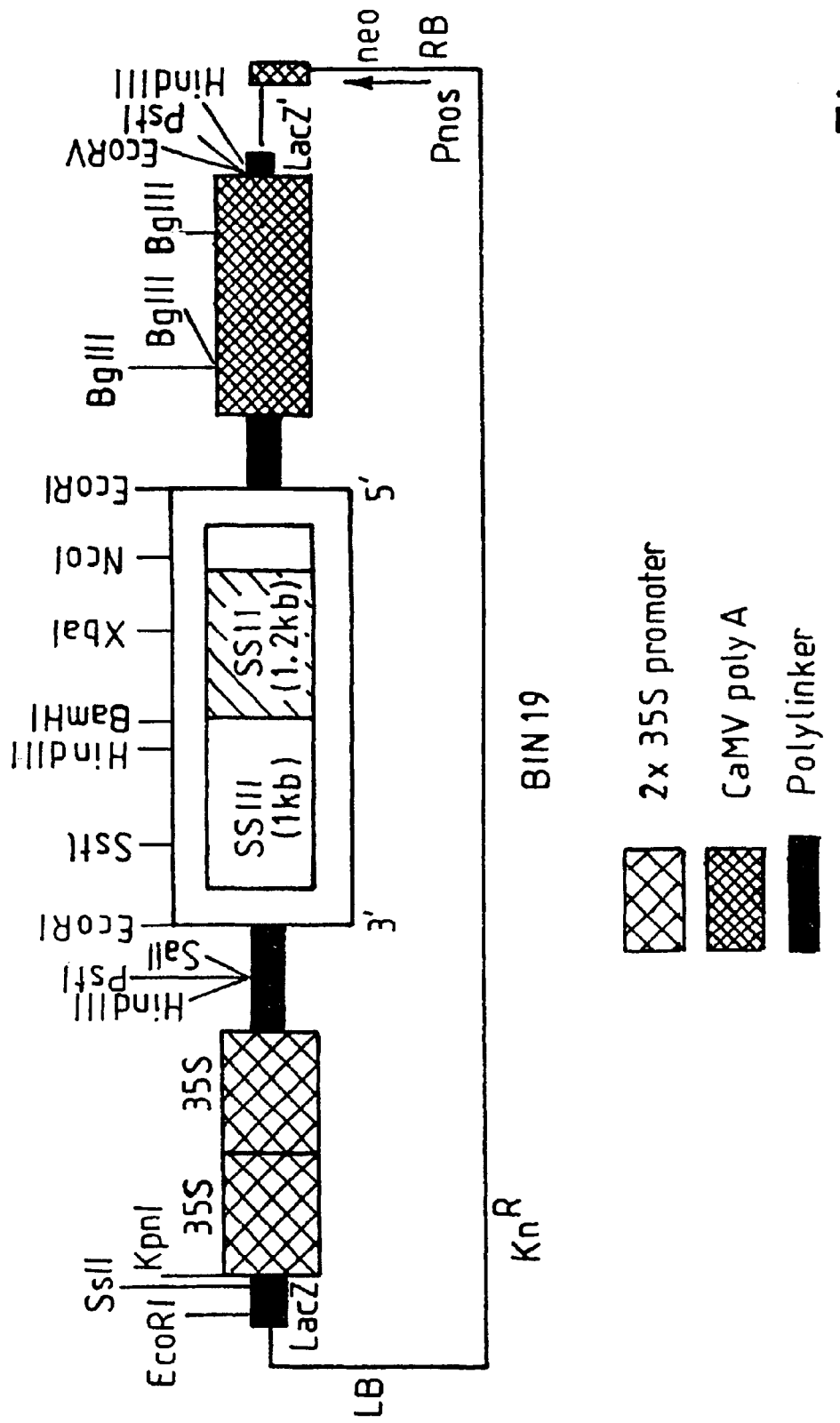
FIG. 6 shows a schematic representation of the double (SSII/SSIII) antisense plant transformation vector plasmid pPOT17.

A double antisense transformation vector containing a partial cDNA for starch synthase II and starch synthase III under the control of the cauliflower mosaic virus double 35S promoter was constructed.

a) A fragment of the potato SSII gene was isolated as a 1.2 kb BglII/BamHI fragment from the full-length cDNA clone for SSII (Edwards et al, 1995; Ac X78988). This fragment was used in the construction of the plasmid used to generate SSII antisense plants.

b) A fragment of the potato SSIII gene was isolated as a 1.14 kb PstI/EcoRV from a partial cDNA clone for SSIII (Marshall et al, 1996; Ac X95759). The SSIII fragment was sub-cloned in an antisense orientation between the cauliflower mosaic virus double 35S promoter and cauliflower mosaic virus terminator (PstI/SmaI sites) in pJIT60 (Guerineau and Mullineaux, 1993 Plant Mol. Biol. Labfax (Croy, ed.) Oxford: Bios Scientific Publishers pp 121–148) producing plasmid pRAT3. The XhoI-partial SstI fragment from pRAT3, encompassing the promoter, antisense cDNA and terminator was ligated between the SalI/SstI sites of the plant transformation vector pBIN19 (Bevan, 1984 Nucl. Acids Res. 12, 8711–8721), resulting in plasmid pRAT4 (Marshall et al, 1996 cited above). This plasmid was used to generate SSIII antisense plants, and is described in EP-A-0779363.

c) The 1.2 kb BglII/BamHI fragment of SSII was cloned, in the antisense orientation, into the BamHI site of pRAT4, to give plasmid pPOT17 (FIG. 6). In this construct, the SSII antisense fragment is flanked by 1 kb of SSIII at the 3' end and 0.14 kb at the 5' end.

2. Transformation of Potato

Binary plasmid pPOT17 was introduced into *Agrobacterium tumefasciens* LBA4404 by the freeze-thaw method of An et al (1988 An G., et al, Binary vectors. In Plant Molecular Biology Manual A3, Gelvin S B, Schilperoot R A, eds (Dordrecht, The Netherlands, Kluwer Academic Publishers) pp 1–19). Preparation of inoculum of Agrobacterium cells carrying pPOT17, inoculation of tuber discs of *Solanum tuberosum* cv Desiree, regeneration of shoots and rooting of shoots were all as described in Edwards et al (1995). Agrobactefium cells were grown in Luria broth containing rifampicin (50 mg l$^{-1}$). The growth medium for the tuber discs was Murashige and Skoog (MS) solution (Murashige and Skoog, 1962 Physiol. Plant 15, 473–479) containing 8 g l$^{-1}$ agar, zeatin riboside (5 mg l$^{-1}$) and indolacetic acid (0.1 mg l$^{-1}$), referred to as MS medium. The discs were co-cultivated for 2 days on tobacco feeder cell layers then transferred to MS medium containing cefotaxime (50 g l$^{-1}$) to select against Agrobacterium. After 5 days the discs were transferred to plates of MS medium containing cefotaxime (50 g l$^{-1}$) and kanamycin (100 mg l$^{-1}$) to select for growth of transformed plant cells.

Shoots were excised from the tuber discs when they had reached a height of at least 1 cm and were rooted on 8 g l$^{-1}$ agar containing hormone-free MS and kanamycin (100 mg l$^{-1}$). Rooted shoots were sub-cultured twice before being transferred to a propagator and then to a greenhouse.

Sampling, extraction and assay of developing tubers for soluble and granule-based starch synthase activity, were carried out following the method of Edwards et al (1995).

C) Starch Analysis

Starch was extracted from potato tubers according to the method described by Edwards et al. (1995), based on that described by Ring et al., (1987 Carbohydrate Research 162, 277–293). Viscoamylograph analysis was performed on an RVA machine (Newport Scientific Series 4) as described in WO 95/26407 and WO 96/34968.

Differential scanning calorimetry was performed as described in WO 95126407 except that larger samples (approx 10 mg) were used. In summary, about 10 mgs of starch powder was accurately weighed into an aluminium sample pan, and water added so that the starch concentration was less than 25% w/v. An empty sample pan was used as a reference. Samples were then analysed in the Perkin Elmer DSC 7 instrument, with a heating rate of 10° C./minute used to raise the temperature of the test samples from 25° C. to 95° C.

Data analysis was performed using the instrument software.

D) Results

Figure 2:
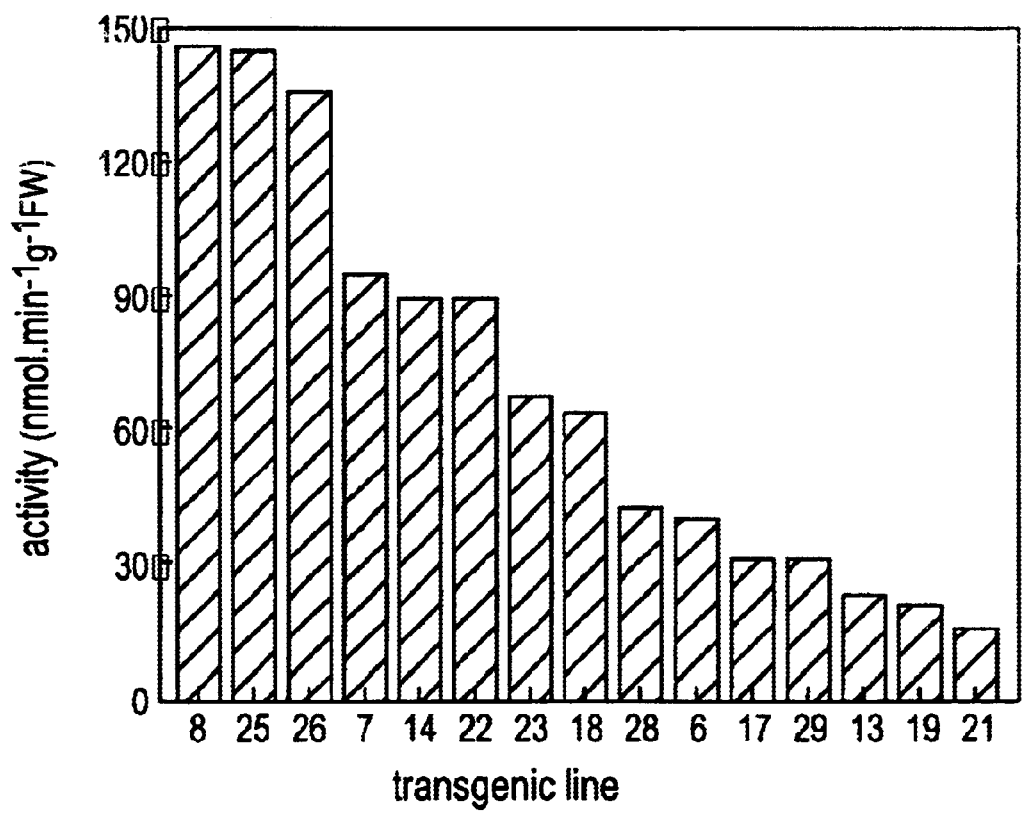
FIG. 2 is a bar chart showing starch synthase activities (nmol.min$^{-1}$ gm$^{-1}$ fresh weight) in SSII/SSIII antisense potato plants. Activities are measurements made on single tubers from independently derived primary transformants. Numbers assigned to these plants and the lines developed from them are indicated at the bottom.

Native polyacrylamide gel electrophoresis (performed according to the method of Edwards et al, 1995) revealed that the activities of both SSII and SSIII isoforms are strongly reduced in the soluble fraction of a number of the developing tubers of the SSII/SSIII antisense plants, an example of which (line 17.21) is shown in FIG. 1, but measurement of soluble starch synthase activity shows that the reduction in activity in these plants is of the same order as, and no greater than, the reduction in soluble starch synthase activity seen in the SSIII antisense plants described previously (Marshall et al 1996) (see FIG. 2 and Table 1 below).

Figure 3A:
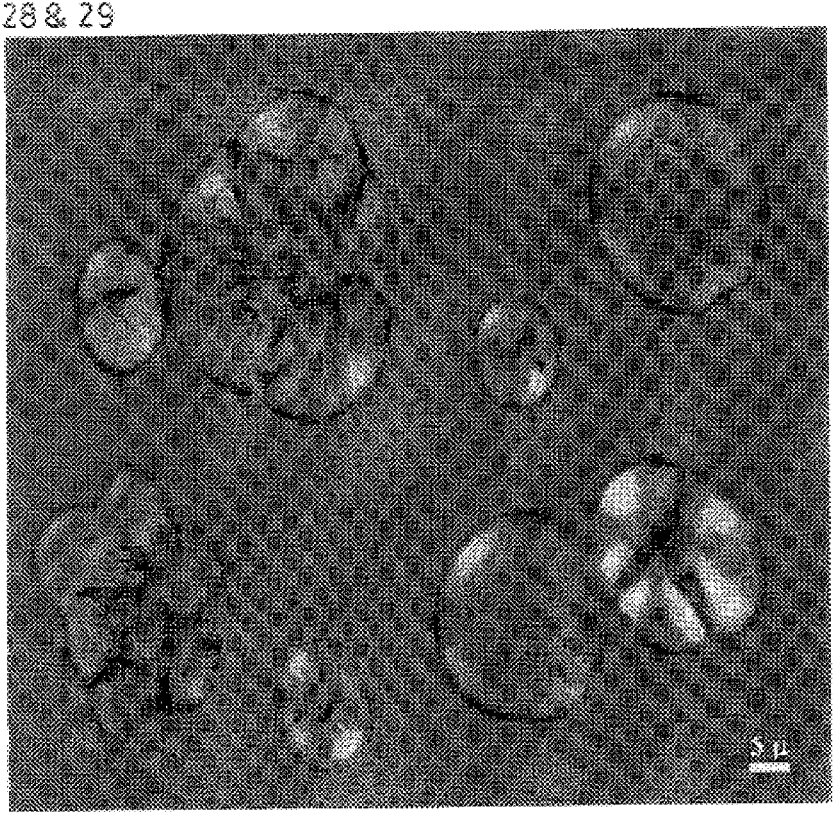
FIGS. 3A and 3B are micrographs illustrating the typical appearance of starch granules extracted from tubers of SSII/SSIII antisense plants (mixture of line 28 and line 29) (3A) and control plants (cultivar Desiree) which are a mixture of line 25 and 26 (3B).
Figure 3B:

The morphology of the starch granules of SSII/SSIII antisense plants is strongly affected, and is distinctly different from the morphology of granules of control or SSIII antisense plants (Marshall et al 1996), FIG. 3). Granules are cracked radially and appear sunk in the centre.

Table 1

Activities of soluble and granule-bound starch synthase in tubers of a low-activity SSII/SSIII antisense line, two independent low-activity SSIII antisense lines (described by Marshall et al, 1996), and a control line (transformed with plasmid BinLuc) containing neither SSII or SSIII antisense sequences. Values are nmol min$^-$g$^{-1}$ FW, and are means±SE of measurements made on 5 separate tubers, taken from at least 2 different plants. All plants were grown in the same greenhouse at the same time and were of comparable age.

| Line | Soluble Activity | Granule-Bound Activity |
| --- | --- | --- |
| SSII/SSIII, line 21 | 29.2 ± 3.6 | 191 ± 17 |
| SSIII, line 9 | 24.4 ± 0.9 | 153 ± 6 |
| SSIII, line 18 | 25.8 ± 1.7 | 155 ± 6 |
| control transformant | 86.9 ± 7.7 | 154 ± 7 |

Figure 4:
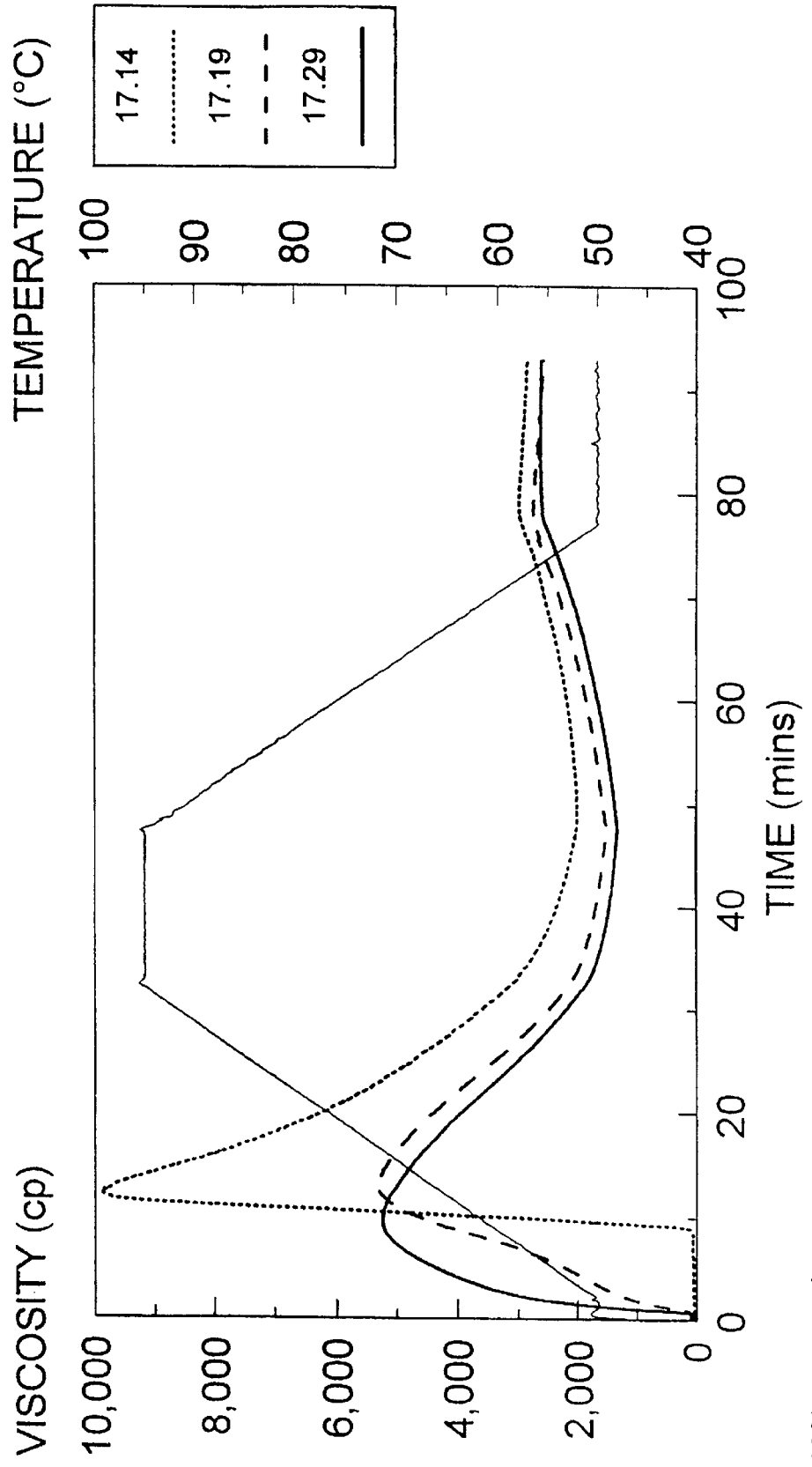
FIG. 4 shows viscoamylographs of 10% suspension of starches from SSII/SSIII antisense lines. Starches were from one line (17.14) in which starch synthase activity was similar to the control (BinG) and two lines in which SSII and III starch synthase activity was reduced (17.29 and 17.19). The unbroken linear trace shows the heating profile. The left hand axis shows viscosity (in centipoise), the right hand axis shows temperature (in ° C.).

The physical properties of the starch are also strongly affected, and very different from those of the SSII or SSIII antisense plants. Viscoamylograph analysis of starch extracted from two, independent transgenic lines, showing approximately equal reductions in soluble starch synthase activity (lines 17.19 [dashed trace] and 17.29 [solid trace], FIG. 4) reveals that swelling of the starch upon heating is very much reduced, and the viscosity onset temperature is at least ten degrees lower than that of starch extracted from untransformed control plants (data not shown) or line 17.14 [dotted trace] which has only a small reduction in starch synthase activity. The viscosity onset temperature of the modified starch, at around 50° C., appears to be the lowest reported for any native starch. Viscosity onset temperatures measured for lines 17.19, 17.29, 17.14 and BinG control were 50.3° C., 50.1° C., 60.3° C. and 61.5° C. respectively.

Figure 5:
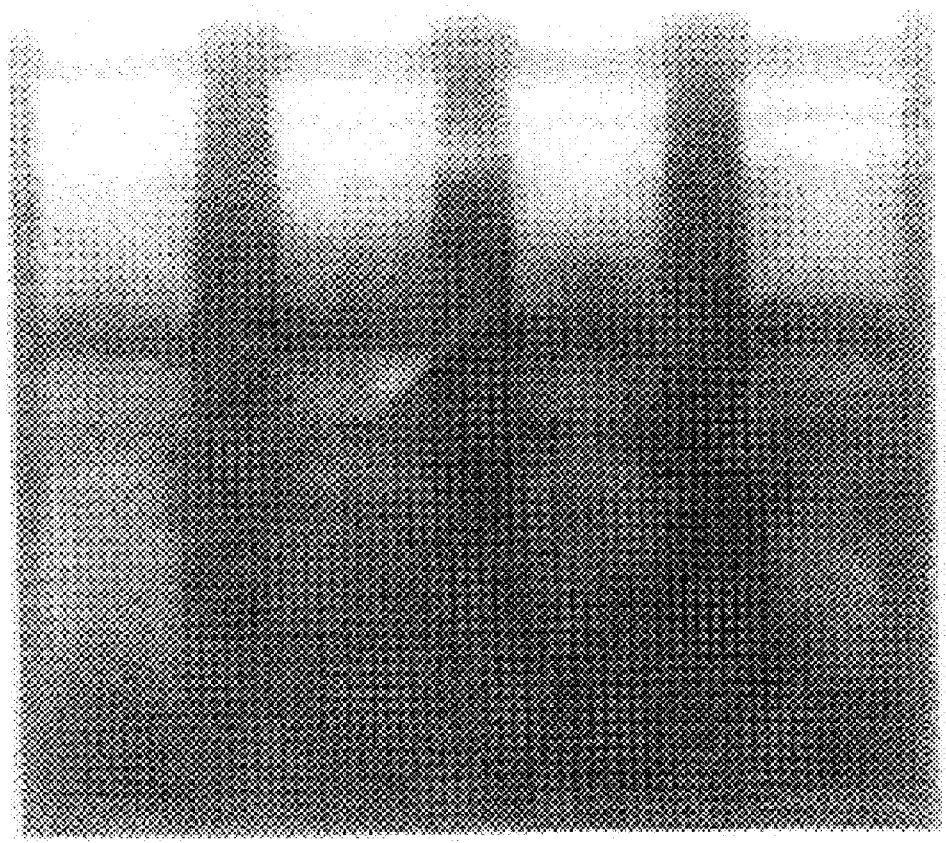
FIG. 5 is a photograph showing the results of native gel electrophoresis developed for activity of starch-hydrolysing enzymes, showing extracts of tubers of (left to right) control line, SSIII antisense (line 9), SSII/SSIII antisense (line 21) and SSII antisense (line 18) potato plants. All lanes contain material extracted from the same fresh weight of tuber.

Biochemical analyses suggest that granule-bound starch synthase activity and the activities of the major starch-hydrolysing enzymes are unaffected in tubers of the SSII/SSIII antisense plants (Tables 1 and 2, FIG. 5).

Table 2

Granule-bound starch synthase activity of starch purified from tubers of a low-activity SSII/SSIII antisense line, two independent low-activity SSIII antisense lines (described by Marshall et at, 1996), and a control line (transformed with plasmid BinLuc). Values are pmol min$^{-1}$ mg$^{-1}$ starch, and are means±SE of values from 4 (BinLuc) or 5 (other lines) preparations of starch, each from a separate tuber. For each line tubers were taken from at least 2 different plants.

| Line | Granule-Bound Activity |
| --- | --- |
| SSII/SSIII, line 21 | 149 ± 14 |
| SSIII, line 9 | 180 ± 10 |
| SSIII, line 18 | 153 ± 12 |
| control transformant | 165 ± 31 |

The physical properties of the starches were further analysed by differential scanning calorimetry. Starches from lines that had both SSII and SSIII significantly reduced (17.19 and 17.29) showed very much lower endotherm onset temperature compared to controls that had wild-type SSII and SSIII activities (lines 17.14 and BinG) (Table 3). These two lines also had much lower enthalpy endotherms.

| Differential Scanning Calorimetry (DSC) | | |
| --- | --- | --- |
| Plant Line | Onset (° C.) | Delta H (J/gm) |
| 17.14 | 59.96 (+/− 0.16) | 21.12 (+/− 0.15) |
| 17.19 | 43.42 (+/− 0.64) | 14.58 (+/− 0.16) |
| 17.29 | 43.72 (+/− 0.30) | 13.95 (+/− 0.04) |
| BinG | 61.51 (+/− 0.13) | 21.43 (+/− 0.25) |

Onset: endotherm onset temperature.
Delta H: endotherm enthalpy.

A determination of apparent amylose content (% w/w) using the iodometric assay method of Morrison & Laigneiet (1983, J. Cereal Sci, 1, 9–20) was performed on starch extracted from a mixture of two independent transgenic lines, showing approximately equal reductions in SSII and SSIII activities (lines 17.28+17.29) and two lines that had wild type SSII and SSIII activities (17.25+17.26). The results are shown in Table 4 and indicate that the modified starch has a slight reduction in the apparent amylose content.

TABLE 4

Apparent Amylose Content

| Plant Line | Apparent Amylose (% w/w) |
|---|---|
| 17.28 + 29 | 24.3% |
| 17.25 + 26 | 28.2% |

The dramatic effects on starch of the simultaneous reduction of SSII and SSIII in potato tubers could not have been predicted from previous knowledge of the nature, roles and properties of the isoforms of starch synthase of the potato tuber, or from knowledge of this class of enzymes in other species of plant. There was no a priori reason to suppose that the effects of reducing both SSII and SSIII would be anything other than those predicted from the effects of reducing these isoforms individually. The lack of effect of reductions in SSII alone on the starch of potato tuber, and the fact that SSII accounts for only 10–15% of the soluble activity of the tuber, would suggest that the starch of a SSII/SSIII antisense plant might not differ radically from that of a SSIII antisense plant, particularly if—as was the case—the total soluble activity was reduced by no more than in the SSIII antisense plants. It might have been reasonable to expect the soluble starch synthase activities lower than those in SSIII might be achieved by reduction of SSII and SSIII together but the effect on starch of such a further reduction in activity could not have been predicted.

Example 2

We describe here an alternative approach to inhibit the expression of two starch synthase genes (SSII and SSIII) in a potato plant.

A) Construction of Plant Transformation Vectors

Figure 7:
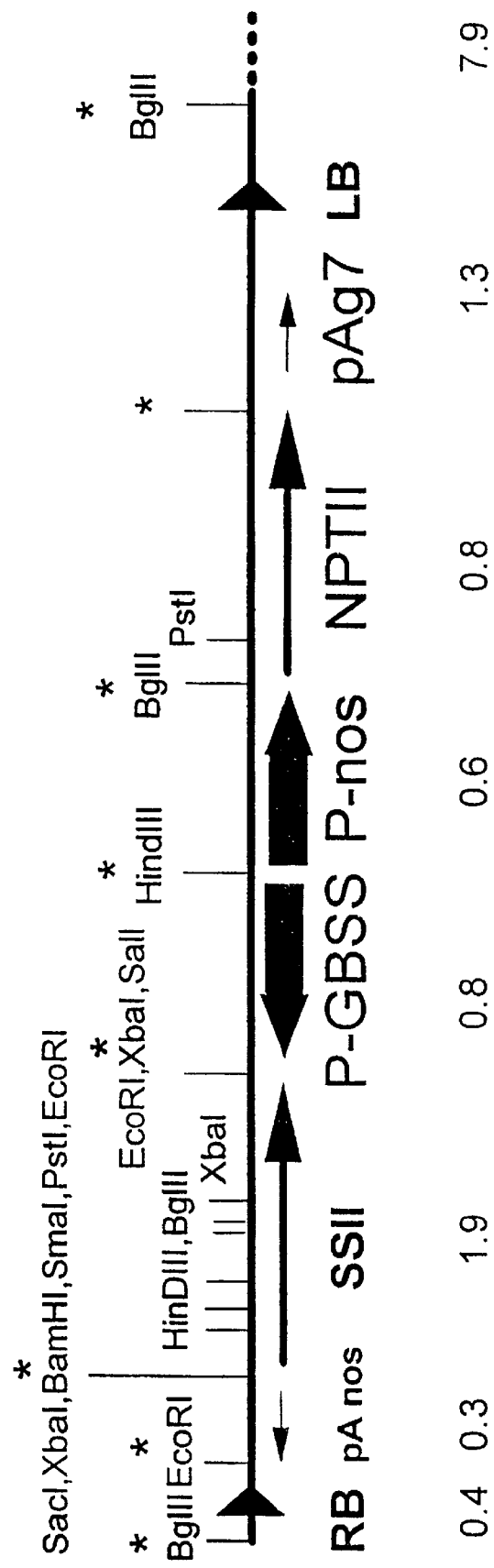
FIG. 7 shows a schematic representation of the SSII antisense plant transformation vector plasmid pSJ42.

A schematic representation of the plant transformation vector (pSJ42) containing a 1.9 kb fragment of potato SSII in an antisense orientation between the GBSS promoter and the NOS polyA signal in a derivative of the binary vector pGPTV-KAN (Becker et al Plant Molecular Biology 20, 1195–1197, 1992) is shown in FIG. 7.

In this figure, the black line represents the DNA sequence. The hashed line represents the bacterial plasmid backbone (containing the origin of replication and bacterial selection marker) and is not shown in full. The filled triangles represent the T-DNA borders (RB=right border and LB=left border). Relevant restriction enzyme sites are shown above the black line with the approximate distances (in kilobases kb) between sites marked by an asterisk shown underneath. The thinnest arrows represent polyadenylation signals (pAnos=nopaline synthase, pAg7=Agrobacterium gene 7), the intermediate arrows protein coding regions (SSII=potato SSII, KAN=kanamycin resistance gene, NPTII) and the thick arrows promoter regions (P-GBSS=potato GBSS and P-nos=nopaline synthase)

This plasmid was constructed as follows. Firstly the BamHI site in pGPTV-KAN was destroyed by filling in with klenow polymerase to create pSJ34. The GUS-nos cassette from this plasmid was removed as a HinDIII-EcoRI fragment and replaced with the HinDIII-EcoRI GBSS promoter/GUS-nos fragment from pGB121 (Visser et al., Plant Molecular Biology 17, 691–699, 1991) to create pSJ40. Finally the 1.9 kb SSII cDNA fragment was removed from POT5 (Dry et al., Plant Journal 2, 193–202, 1992) as a SacI-EcoRV fragment and inserted into the SacI-SmaI sites of plasmid pSJ40 to create pSJ42.

Figure 8:
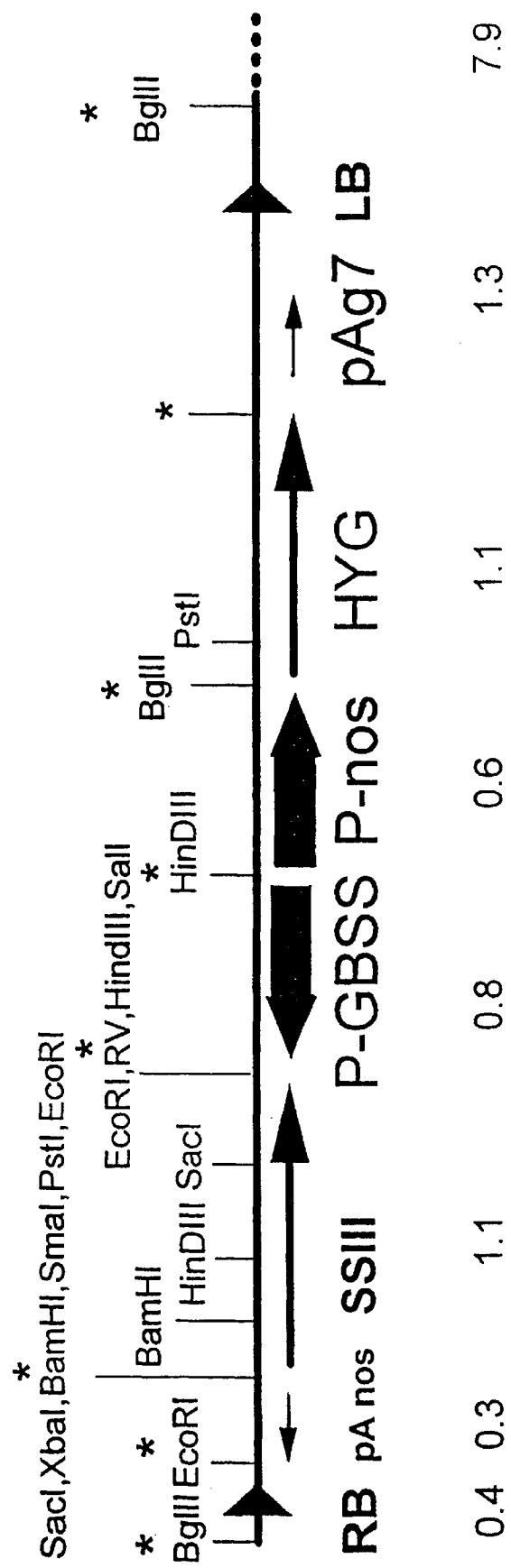
FIG. 8 shows a schematic representation of the SSIII antisense plant transformation vector plasmid pSJ119.

A schematic of the plant transformation vector pSJ119 containing a 1.1 kb fragment of potato SSIII in an antisense orientation between the GBSS promoter and the NOS polyA signal in a derivative of the binary vector pGPTV-HYG (Becker et al Plant Molecular Biology 20, 1195–1197, 1992) is shown in FIG. 8.

In this figure, the black line represents the DNA sequence. The hashed line represents the bacterial plasmid backbone (containing the origin of replication and bacterial selection marker) and is not shown in full. The filled triangles represent the T-DNA borders (RB=right border and LB=left border). Relevant restriction enzyme sites are shown above the black line with the approximate distances (in kilobases kb) between sites marked by an asterisk shown underneath. The thinnest arrows represent polyadenylation signals (pAnos=nopaline synthase, pAg7=Agrobacterium gene 7), the intermediate arrows protein coding regions (SSIII=potato SSIII, HYG=hygromycin resistance gene) and the thick arrows promoter regions (P-GBSS=potato GBSS and P-nos=nopaline synthase).

This plasmid was constructed as follows. Firstly the BamHI site in pGPTV-HYG was destroyed by filling in with klenow polymerase to create pSJ35. The GUS-nos cassette from this plasmid was removed as a HinDIII-EcoRI fragment and replaced with the HinDIII-EcoRI GBSS promoter GUS-nos fragment from pGB121 (Visser et al., Plant Molecular Biology 17, 691–699, 1991) to create pSJ39. The 1.9 kb SSII cDNA was removed from POT5 (Dry et al., cited above) as a SacI-EcoRV fragment and inserted into the SacI-SmaI sites of plasmid pSJ39 to create pSJ43. The 1.1 kb SSIII cDNA EcoRI fragment from pRAT4 (Marshall et al., Plant Cell 8, 1121–1135, 1996) was subcloned into pBSSKIIP (Stratagene) to create pSJ110 and then subsequently cloned as an XbaI-SalI fragment into the same sites of plasmid pSJ43 to create pSJ119.

B) Transformation of Potato Plants and Starch Analysis

This was as described in WO 95/26407 and WO 96/34968, except for the DSC analysis of the "04" starches which was performed as described in Example 1. Western analysis and starch synthase zymograms were performed as described previously (Edwards et al, Plant J. 8, 283–294, 1995).

C) High Performance Anion Exchange Chromatography (HPAEC)

Starch granules were dissolved in dimethyl sulphoxide and precipitated with ethanol. The precipitated material was collected by centrifugation, washed twice with ethanol and concentrated with acetone before vacuum drying overnight in a dessicator. To prepare debranched samples, each sample (20 mg) was weighed into a 10 ml vial. Two ml of aqueous DMSO (DMSO:water, 9:1 v/v) was added, the sample mixed with a stirring bar and heated in a boiling water bath for 15 minutes. After cooling to room temperature, 6.98 ml of 50 mM sodium acetate buffer pH 4.8 was added and mixed before addition of isoamylase (Pseudomonas amyloderamosa, Hayashibara Biochemical Laboratories, Inc. Okayama, Japan) (120 units) and incubation for 16 hr at 38° C. One ml of 150 mM NaOH was added and after mixing 1 ml was then used for HPAEC analysis as described below.

Chain-length distribution of the debranched starches was determined by HPAEC with pulsed amperometric detection (Dionex Corp., Sunnyvale, Calif.). A Dionex Carbopac PA-100 column (4×25 mm) was used with a Carbopac PA Guard column (3×25 mm). The potential and time settings on the PAD cell were: $E_r=0.10$ ($t_1=480$); $E2=0.60$ ($t_2=120$); $E3=-0.80$ V ($t_3=300$ ms). The eluent A was 150 mM sodium hydroxide solution which was prepared by dilution of carbonate-free sodium hydroxide in deionised water. The eluent B was 150 mM sodium hydroxide solution containing 500 mM sodium acetate. The gradient programme is shown in the table below. All separations were carried out at ambient temperature at a flow rate of 1 ml/minute. The data are presented as a percentage of total peak area without regard for changes in detector response which varies with chain length.

| Time min | 0 | 0.1 | 0.4 | 20 | 35 | 50 | 75 | 85 | 87 | 95 | 105 |
|---|---|---|---|---|---|---|---|---|---|---|---|
| A | 85 | 85 | 85 | 65 | 50 | 40 | 30 | 25 | 0 | 85 | 85 |
| B | 15 | 15 | 15 | 35 | 50 | 60 | 70 | 75 | 100 | 15 | 15 |

D) Gel Permeation Chromatography

A Water Associates (Milford, Mass.) GPC-150 model with refractive index (RI) detector was used to determine molecular weight distribution. Two PL gel columns ($10^5$ and $10^3$) made of highly crosslinked spherical polystryene/divinylbenzene, were obtained from Polymer laboratories (Amherst, Mass.) and connected in sequence. Dextrans from American Polymer Standards (Mentor, Ohio) were used as size standards. Columns were run at 80° C. at a flow rate of 1 ml/min with a mobile phase of dimethyl sulfoxide in 5 mM sodium nitrate with a sample concentration of 1.25 mg/ml (dissolved in mobile phase and boiled for 3 hours with stirring) and an injection volume of 300 gl.

E) Results

One potato line (plant 118) which was transformed with the antisense SSII construct showed a significant decrease in SSII expression on western blots and by starch synthase zymogram assay and was selected for further study. Starch extracted from greenhouse grown tubers of this plant showed altered physical properties. The onset of gelatinisation as measured by differential scanning calorimetry (DSC) and the onset of viscosity in RVA (rapid viscometric analysis) were significantly less than controls (107 and 124) and other antisense plants that did not show any alteration in SSII expression (112–133) (Table 5).

In addition the swelling properties of the SSII antisense line 118 starch was characterised mainly by having a lower, broader peak than the controls. Upon regrowth the shape of the viscosity profile was maintained but the onset of viscosity development was slightly higher than controls and the setback viscosity was also slightly higher (see 0402, FIG. 9). However when line 118 was regrown from tubers, starch extracted from these tubers showed properties similar to the original line (data not shown).

TABLE 5

DSC analysis of SSII antisense starches

| Plant | DSC onset ° C. | RVA onset ° C. |
|---|---|---|
| 107(control) | 63.4 | 64.6 |
| 124(control) | 63.7 | 66.2 |
| 118 | 59.8 | 63.2 |
| 112 | 62.6 | 64.6 |
| 120 | 63.7 | 66.0 |
| 123 | 63.4 | 66.0 |
| 127 | 61.0 | 64.1 |
| 129 | 62.1 | 64.6 |
| 133 | 61.6 | 64.8 |

Line 118 was maintained in tissue culture and then retransformed with the pSJ119 antisense SIII construct. Hygromycin resistant, and therefore doubly transformed plants, were grown to maturity and tubers were harvested for analysis of starch synthase activity and starch extracted. Six plants (0412–0445) showed a complete or almost complete reduction in SSIII activity compared to the SSII antisense lines (0403 and 0405) as evidenced by an absence of the uppermost band corresponding to SSIII in starch synthase zymograms (data not shown).

Figure 9:
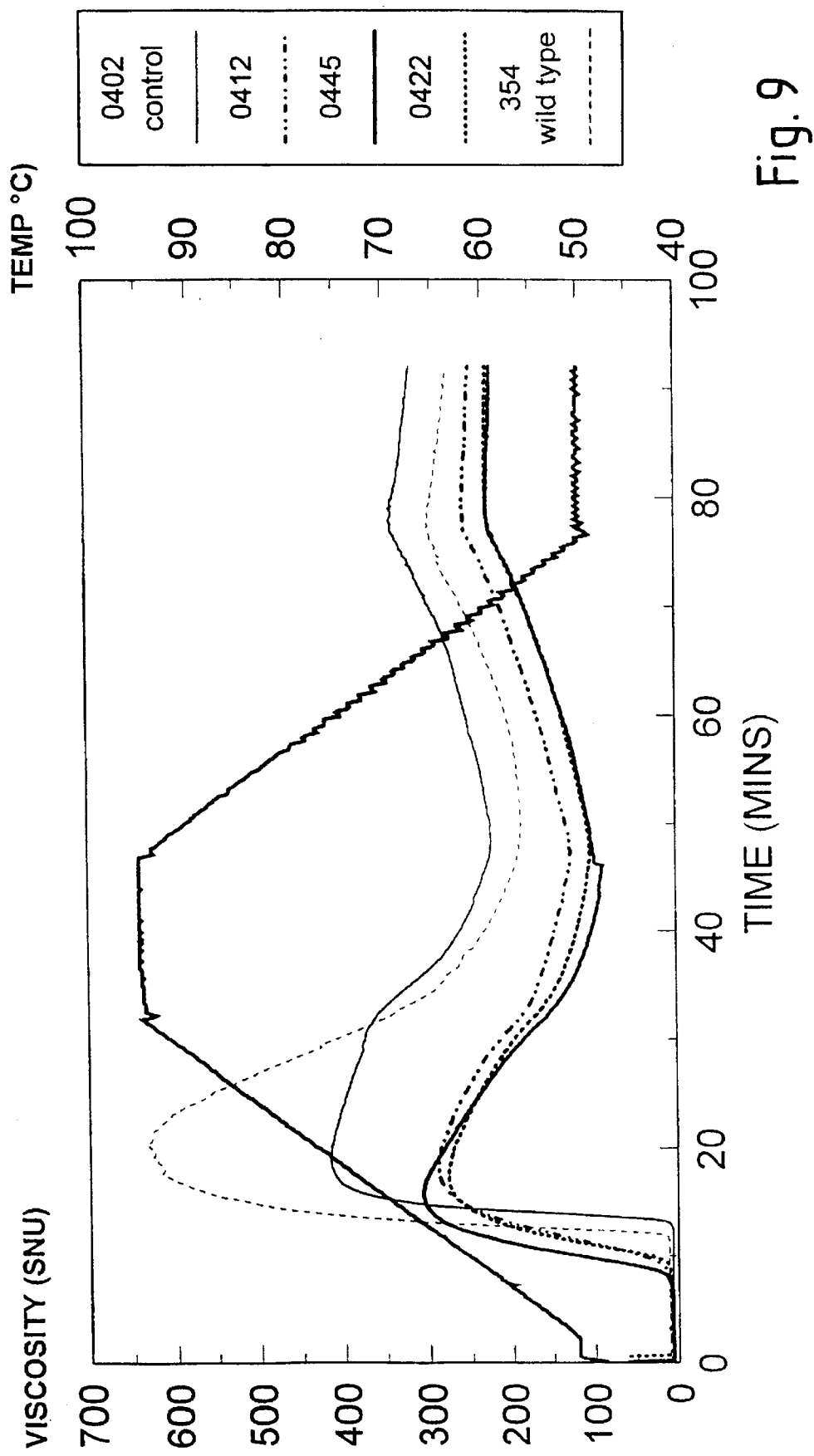
FIG. 9 shows viscoamylographs of 10% suspensions of starches from SSII and SSIII double transformed antisense lines. Starches were from one line (0402) in which only starch synthase II was reduced compared to the wild type (354) and three lines in which both SSII and III starch synthase activity was reduced (0412, 0422 and 0445). The left hand axis shows viscosity (in "Stirring Number Units") and the right hand axis shows temperature in ° C.

The swelling properties of the SSII and III antisense starches (0412–0445) were dramatically altered; these starches started to swell at much lower temperatures than the controls and also had lower peak viscosities and setback (FIG. 9). The most highly-modified starches, 0412 and 0445, exhibited viscosity onset temperatures of 59.2 and 57.6° C. spectively whereas the controls 0401 and 0402 had viscosity onset temperatures of 68.0 and 66.0° C.

DSC analysis provided further evidence that the structure of these starches was dramatically altered: these starches showed large reductions in the onset of gelatinisation and peak temperatures of up to 17.5° C. and 12° C. respectively compared to the SSII antisense lines (0403, 0405) or a double transformed line in which no reduction in SSIII had occured (0455) (Table 6). In addition, the starches showed a lower enthalpy endotherm ($\Delta H$).

TABLE 6

DSC SSII and SSIII antisense starches

| Plant | DSC peak ° C. | Delta H DSC J/gm | onset DSC ° C. |
|---|---|---|---|
| 0403 | 68.6 | 22.1 | 64.1 |
| 0405 | 71.1 | 22.4 | 66.4 |
| 0412 | 58.0 | 17.4 | 48.1 |
| 0415 | 61.5 | 19.4 | 51.8 |
| 0422 | 60.8 | 20.3 | 52.9 |
| 0425 | 63.1 | 18.5 | 51.9 |
| 0444 | 62.9 | 19.2 | 55.2 |
| 0445 | 59.7 | 17.4 | 50.9 |
| 0455 | 70.4 | 22.4 | 66.2 |

Figure 10:
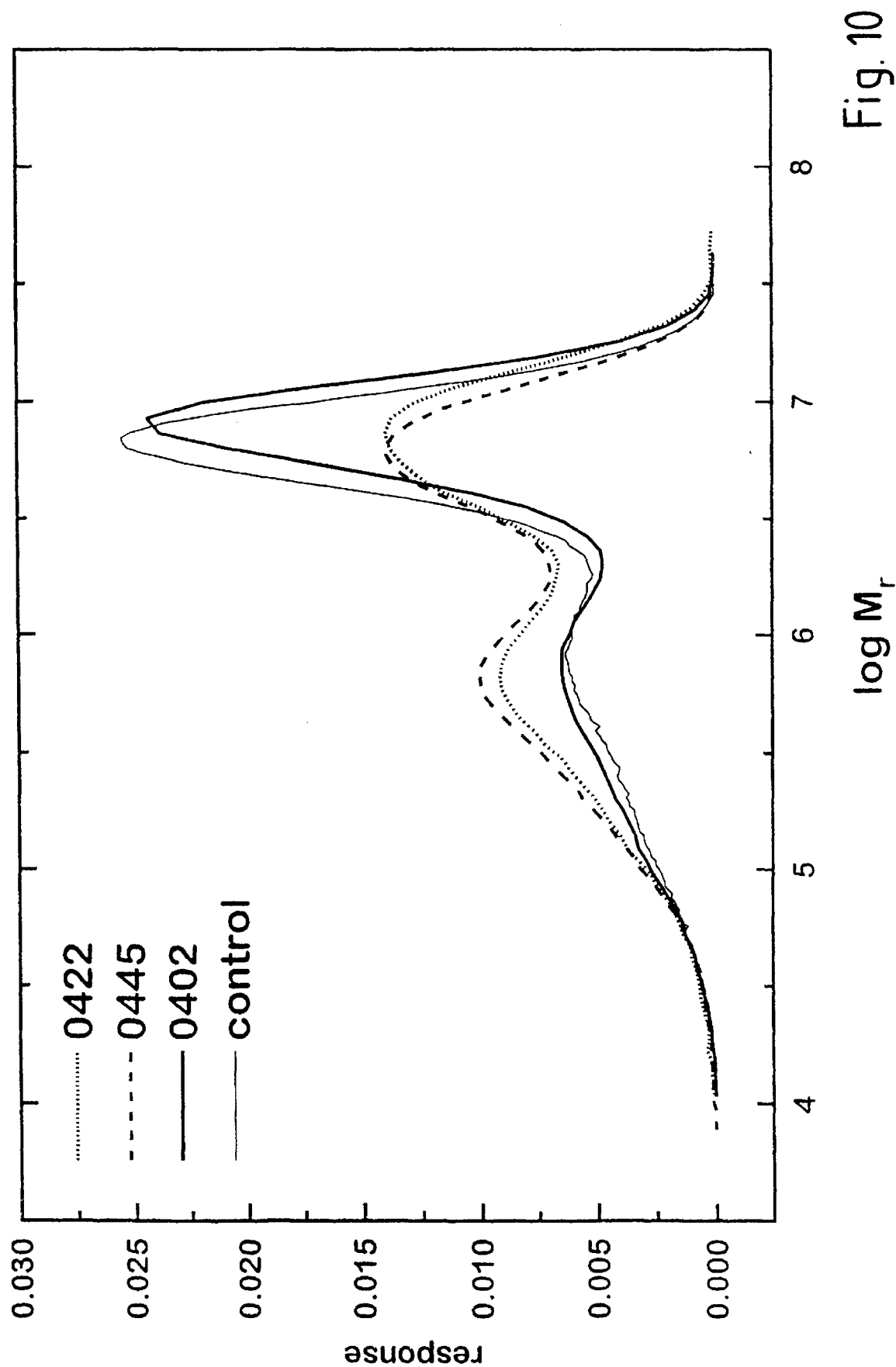
FIG. 10 is a graph (response against log $M_r$) showing the results of gel permeation chromatography of starches from SSII and SSIII double transformed antisense lines. Starches were from one line (0422) in which only starch synthase II was reduced and two lines in which both SSII and III starch synthase activity was reduced (0412 and 0445) compared to the control.

The 0402, 0422 and 0445 starches were characterised in more detail to determine what changes had occurred in the molecular structure. Gel permeation chromatography of the starches resulted in a clear separation of the amylose and amylopectin components of the strach (FIG. 10). The larger amylopectin fraction eluted first at a molecular mass of approximately $10\times10^7$ whereas the broader amylose fraction had a much smaller mass of between $10^5$–$10^6$. The 0402 control (thick solid trace), in which only the SSII activity was reduced, had a very similar profile to the wild type control (data not shown). In contrast the profile of the two starches with SSII and SSIII reduced (0422, dotted trace; 0445 dashed trace) was dramatically altered in that they both displayed a reduced amylopectin peak, and the amylose peak was increased significantly: integration of the areas under the respective peaks showed that the amylose/amylopectin content of 0445 starch was about 51%/49%, whereas that of 0402 starch was about 37% amylose, 63% amylopectin.

Figure 11:
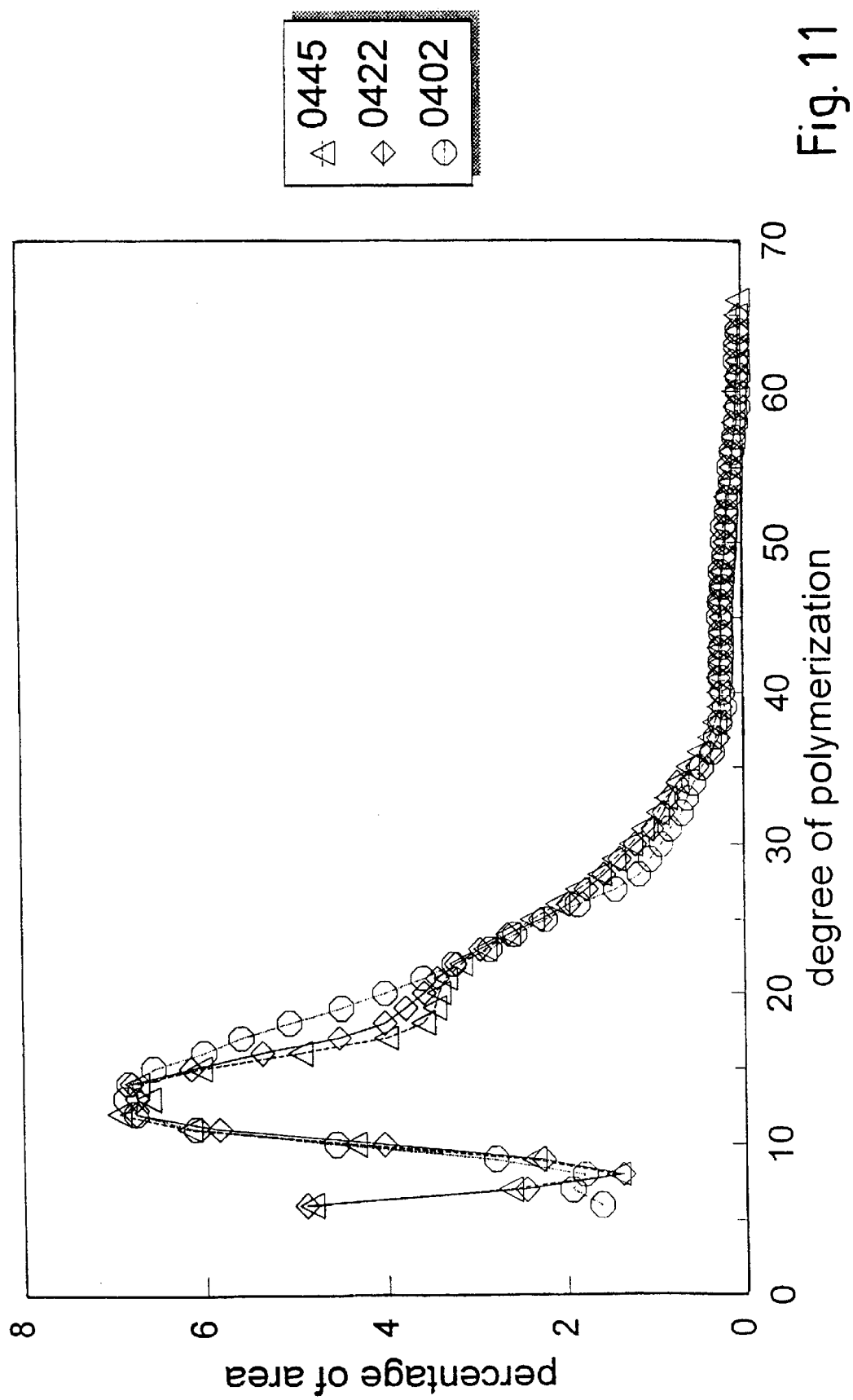
FIG. 11 is a graph (percentage of area under curve against DP) showing the chain length distribution of starches from SSII and SSII double transformed antisense lines. Starches were from one line (0422) in which only starch synthase II was reduced and two lines in which both SSII and III starch synthase activity was reduced (0412 and 0445).

The chain length distribution of the starches after enzymatic debranching with isoamylase was also examined by high performance anion exchange chromatography (HPAEC). The 0402 control (circular symbols) showed a chain length distribution characteristic of wild type potato (data omitted for brevity, see Hanashiro et al., Carbohydrate Research 283, 151–159, 1996) with a small hollow at DP(degree of polymerisation)8 and a large peak at DP12–13 (see FIG. 11). There were big changes in the chain length distribution in the 0422 (lozenge symbols) and 0445 (trianngular symbols) starches. They both showed a large (about 2 fold) increase in short chains (DP6&7) compared to the 0402 control. In addition the chain length profile of these starches had a distinctive shoulder to the peak, indicating a depletion of chains of between DP15–20 compared to the 0402 control. Such a chain length distribution has not been previously described for potato starch.

Example 3

The molecular characteristics of starch from line 17.29 were examined in more detail using methods as described in example 2 and as described by Shi et al (1998 J. Cereal Sci. 27, 289–299). Plants from line 17.29 were multiplied in tissue culture and grown in pots in the greenhouse together with control (wild type) plants. Starch was extracted from mature tubers as described previously. Plants from line 17.29 were identified by the number 1807 and control plants by the number 1603.

Figure 12:
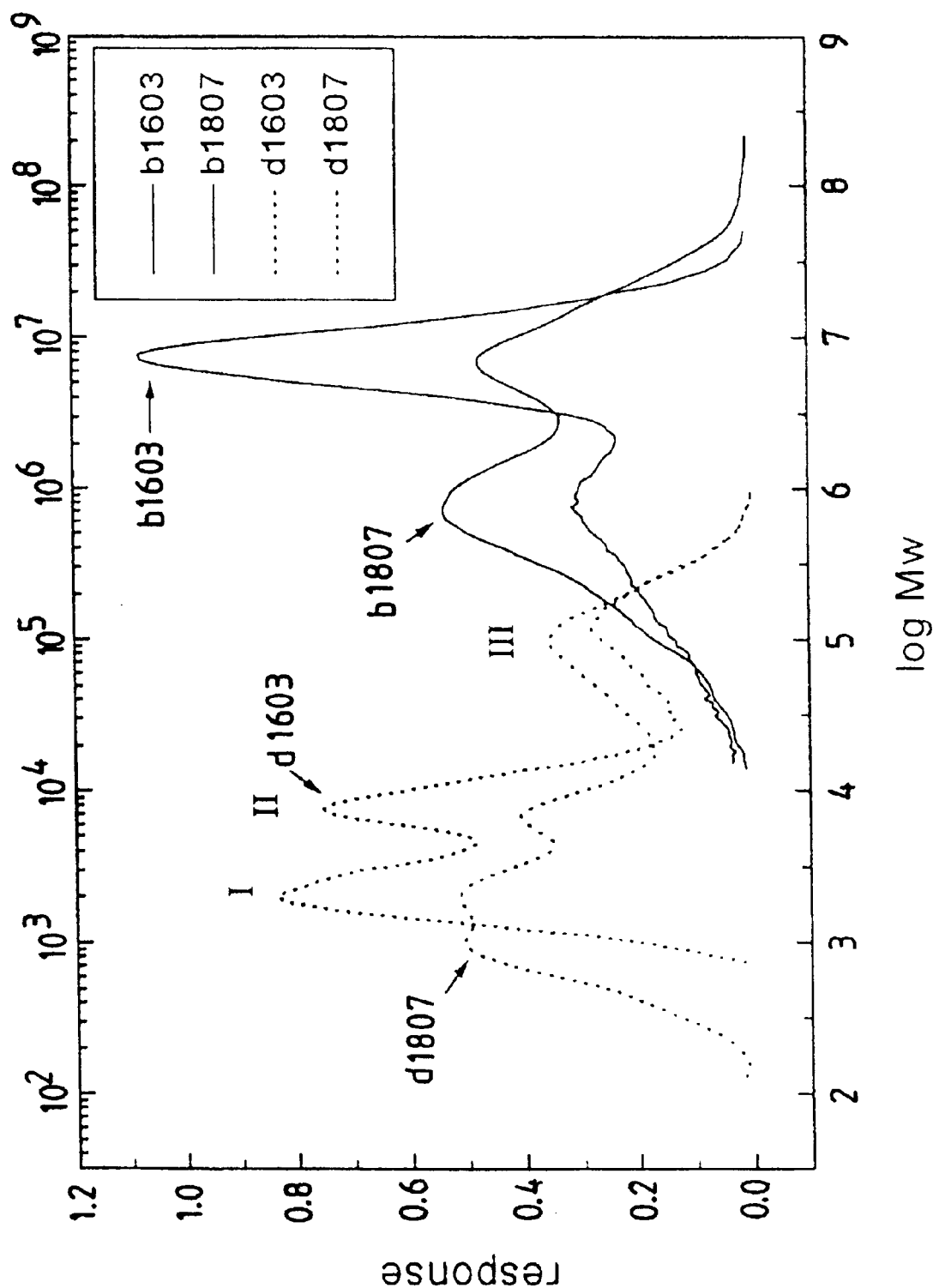
FIG. 12 is a graph (of response against log $M_w$) showing the results of gel permeation chromatography of native starch (unbroken curves) or debranched starch (dotted curves) from a plant (1807) in which SSII/SSIII activity was reduced and from a control plant (1603).

Gel permeation chromatography (results shown in FIG. 12, Solid traces) of the native starches showed that the composition of starch from plants of line 1807 was very different from that of the control 1603 starch and similar to that of line 0422 and 0445 starches (compare FIG. 12 with example 2, FIG. 10). The amylose containing peak of line 1807 (approx $10^5$–$10^6$ molecular size) was much increased compared to the control and the amylopectin much decreased.

The molecular structure of the starches was also examined after debranching of the starch with isoamylase since this provides information on the proportion and size of the linear chains within amylose and amylopectin fractions. The control starch showed a typical profile with a bimodal peak of smaller chains ($10^3$–$10^4$ size) and single peak of larger linear chains of approximately $10^5$ molecular size; these were designated as peak I, II and III respectively (FIG. 12, dotted traces). Peaks I and II are mainly derived from amylopectin and peak III from the amylose fractions. Starch from line 1807 showed a dramatically altered distribution with the proportion of chains in peak II decreasing significantly compared to the control (1603) and there were more chains of less than $10^3$ size in peak I. Integration of the areas under the peaks (in order of increasing size) gave values of 41.4%, 35.0% and 23.7% for the control and 47.8%, 18.7% and 33.3% for line 1807 starch. Thus the ratio of the first two peaks had changed from 54%:46% in the control to 72%:28% in line 1807. The proportion of linear chains of approx $10^5$ molecular size was also increased in line 1807 (from 23.7% to 33.3%) indicating that the amylose content of the 1807 starch was increased compared to the control.

Figure 13:
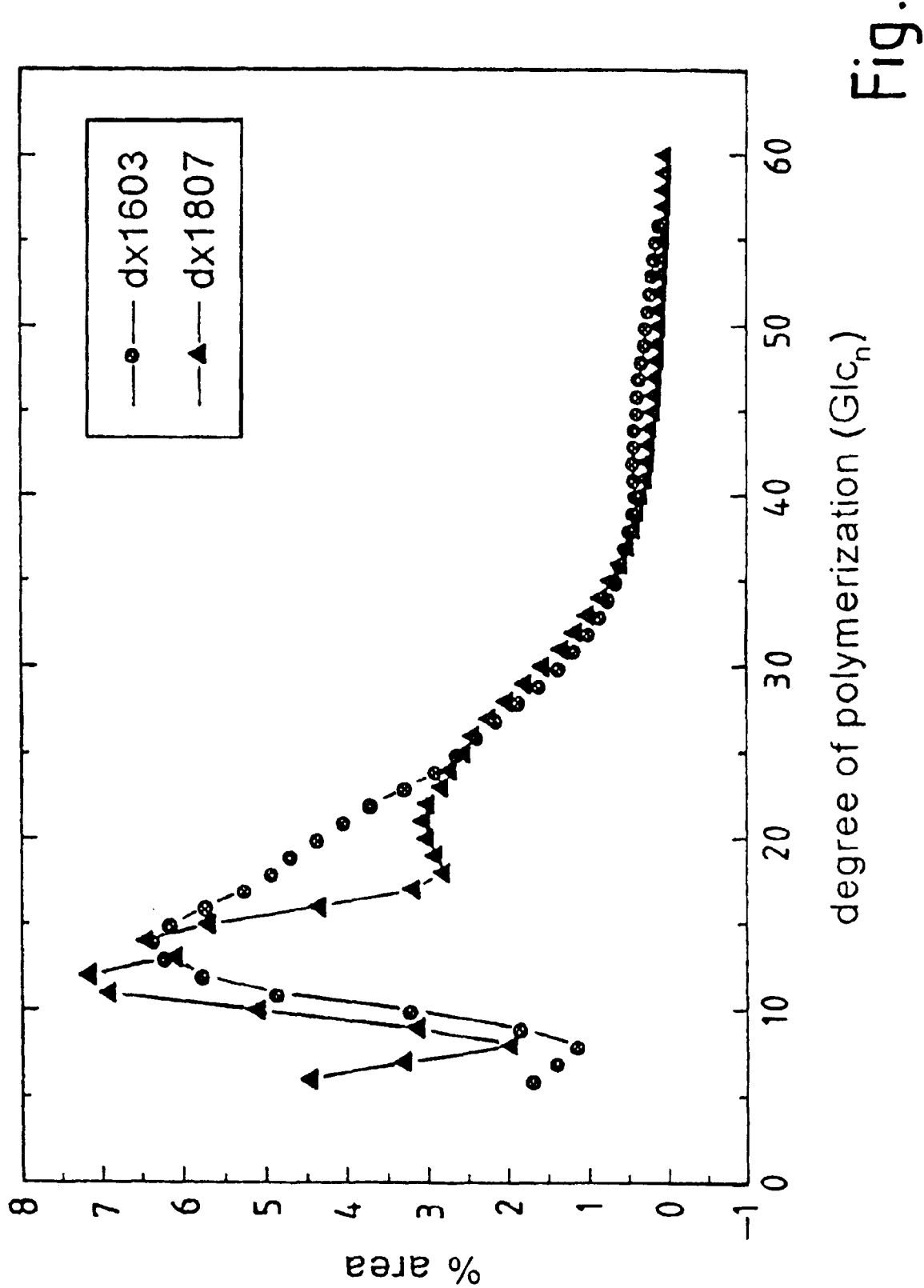
FIG. 13 is a graph (percentage of area under curve against DP) showing the chain length distribution of starches as analysed by HPAEC. The results for starch from a control plant (1603) are denoted by circular symbols, whilst those for starch from an SSII/SSIII antisense plant (1807) are denoted by triangles.
Figure 14:
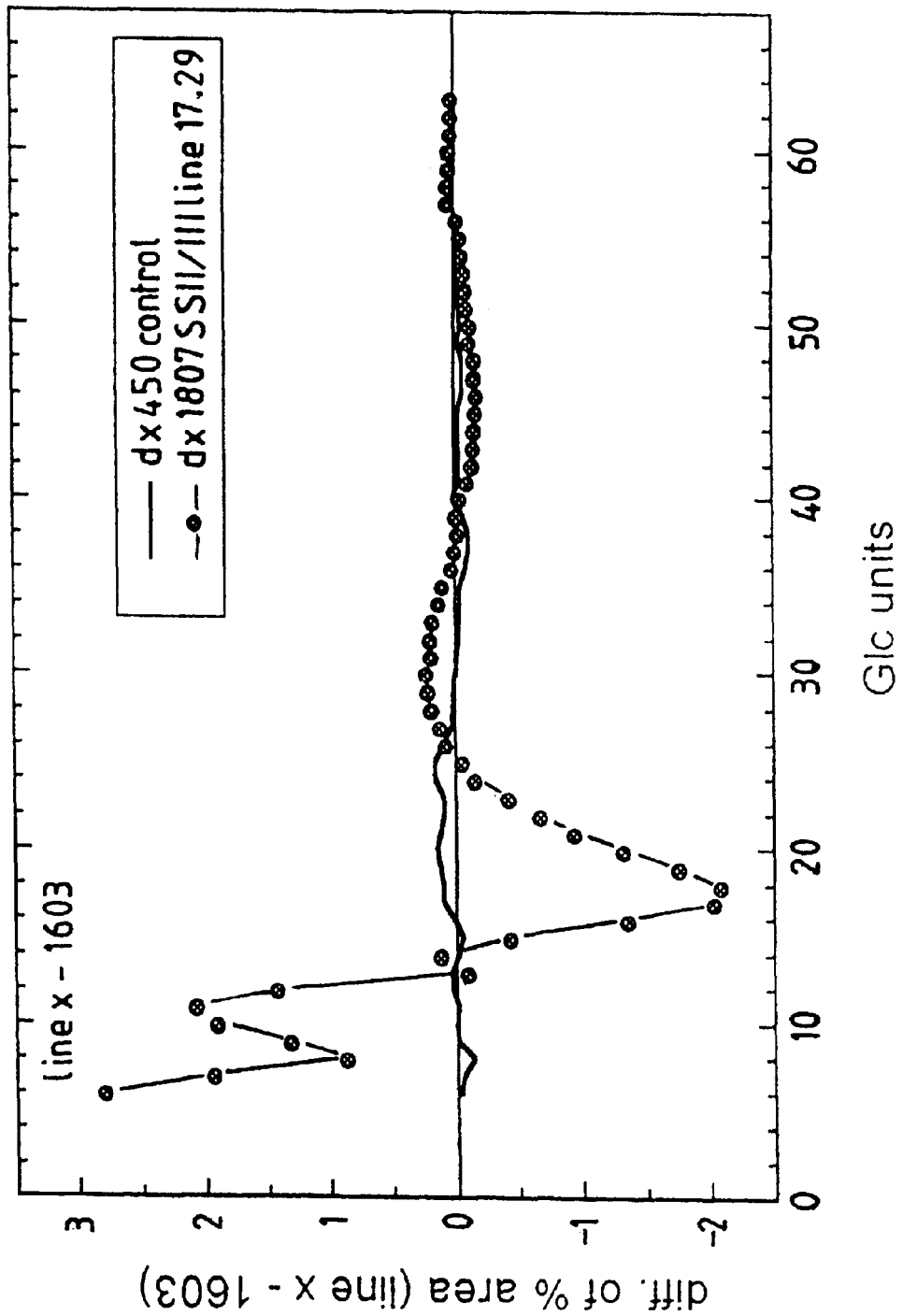
FIG. 14 is a graph (of difference in % area under curve relative to control, against DP) illustrating in a different format the data shown in FIG. 13. The mid-point on the vertical scale indicates exact correspondence with the characteristics of starch from control plant 1603. Results for starch from another control plant (450) are included (thick black curve) to show the reproducibility of the technique. Results for starch from a plant with reduced SSII/SSIII activity (1807) are shown by the curve with circular symbols.

The chain length distribution of these starches was further examined by HPAEC using the dionex system as described in example 2 above, and the results are shown in FIG. 13. The chain length distribution of line 1807 (triangular symbols) was dramatically altered compared to the control 1603 starch (circular symbols) and was broadly similar to that of starch from lines 0422 and 0445 (described in example 2). The control starch has a minimum at DP 8 and a maximum at dp14. Starch from line 1807 had a greatly increased number of short chains (DP 6–12) and a shift in the chain distribution towards shorter chains so that the peak chain length was at DP 12. A further significant change was a decrease in the chain length of DP 15–24 with a minimum at DP 18. These changes are more easily seen when the results are shown as a difference plot (FIG. 14). This figure was produced by subtracting the % area of each peak in the control from the selected sample data. For comparison, a further control (designated as 450) is also shown, giving an indication of the reproducibility of the chain length distribution as determined by this technique.

What is claimed is:

1. Starch extracted from a plant that has been stably transformed with at least two heterologous nucleic acid sequences, wherein each nucleic acid sequence encodes a different starch synthase enzyme, wherein the starch has a viscosity onset temperature, as judged by viscoamylograph of a 10% w/w aqueous suspension at atmospheric pressure wherein the temperature is reduced by at least about 12° C. compared to starch extracted from equivalent, unmodified plants.

2. Starch extracted from a plant that has been stably transformed with at least two heterologous nucleic acid sequences, wherein each nucleic acid sequence encodes a different starch synthase enzyme, wherein the starch has an endotherm onset temperature, as determined by differential scanning calorimetry, which is reduced by at least about 15° C. compared to starch extracted from equivalent, unmodified plants.

3. Starch extracted from a plant that has been stably transformed with at least two heterologous nucleic acid sequences, wherein each nucleic acid sequence encodes a different starch synthase enzyme, wherein the starch has an endotherm onset temperature, as determined by differential scanning calorimetry, which is reduced by at least about 17° C. compared to starch extracted from equivalent, unmodified plants.

4. Starch extracted from a plant that has been stably transformed with at least two heterologous nucleic acid sequences, wherein the starch has an increased amount of starch molecules with a degree of polymerisation of 6–12, as judged by analysis of debranched starch by high performance anion exchange chromatography (HPAEC), compared to starch extracted from equivalent, unmodified plants.

5. Starch extracted from a plant that has been stably transformed with at least two heterologous nucleic acid sequences, wherein each nucleic acid sequence encodes a different starch synthase enzyme, wherein the starch has a decreased amount of starch molecules with a degree of polymerisation of 15–24, as judged by analysis of debranched starch by HPAEC column, compared to starch extracted from equivalent, unmodified plants.

6. Starch extracted from a plant that has been stably transformed with at least two heterologous nucleic acid sequences, wherein each nucleic acid sequence encodes a starch synthase enzyme, wherein the starch has about a two fold increase in starch molecules with a degree of polymerization of 6–7 and a depletion of starch molecules with a degree of polymerization between 15–20, as judged by analysis of debranched starch by HPAEC, compared to starch extracted from equivalent, unmodified plants.

7. Starch extracted from a plant that has been stably transformed with at least two heterologous nucleic acid sequences, wherein each nucleic acid sequence encodes a starch synthase enzyme, and wherein the starch has an endotherm onset temperature, as judged by differential scanning calorimetry, of less than about 50° C.

8. Starch according to claim 7, having an endotherm onset temperature of less than about 44° C.

9. The starch according to any one of claims 1–6 and 7–8, wherein the two heterologous nucleic acid sequences encode potato starch synthase II (SSII) enzyme and potato starch synthase III (SSIII) enzyme.

* * * * *

UNITED STATES PATENT AND TRADEMARK OFFICE
CERTIFICATE OF CORRECTION

| | | |
|---|---|---|
| PATENT NO. | : 6,635,756 B1 | Page 1 of 1 |
| APPLICATION NO. | : 09/719771 | |
| DATED | : October 21, 2003 | |
| INVENTOR(S) | : Stephen A. Jobling et al. | |

It is certified that error appears in the above-identified patent and that said Letters Patent is hereby corrected as shown below:

On Title Page, Item (30)

<u>Foreign Application Priority Data</u>
Replace "98309716" with --98304716.8--.

Signed and Sealed this

Nineteenth Day of December, 2006

JON W. DUDAS
*Director of the United States Patent and Trademark Office*